(12) United States Patent
Fox

(10) Patent No.: US 7,303,715 B1
(45) Date of Patent: Dec. 4, 2007

(54) HORIZONTAL GEL CASTING DEVICE AND METHOD

(75) Inventor: Gregory S. Fox, North Reading, MA (US)

(73) Assignee: Owl Separation Systems, Inc., Portsmouth, NH (US)

( * ) Notice: Subject to any disclaimer, the term of this patent is extended or adjusted under 35 U.S.C. 154(b) by 621 days.

(21) Appl. No.: 10/309,914

(22) Filed: Dec. 4, 2002

(51) Int. Cl.
*B29C 39/02* (2006.01)
*B29C 39/04* (2006.01)

(52) U.S. Cl. .................. 264/299; 264/219; 425/470

(58) Field of Classification Search ............. 264/219, 264/299
See application file for complete search history.

(56) References Cited

U.S. PATENT DOCUMENTS

| | | | | |
|---|---|---|---|---|
| 1,436,044 A | * | 11/1922 | Manton et al. ............... | 276/41 |
| 3,803,020 A | * | 4/1974 | Stephan .................... | 422/82.01 |
| 4,151,065 A | | 4/1979 | Kaplan et al. ............... | 204/299 |
| 4,234,400 A | * | 11/1980 | Kaplan et al. ............... | 204/461 |
| 4,588,491 A | | 5/1986 | Kreisher et al. ............. | 204/299 |
| 4,618,408 A | * | 10/1986 | Malavarca et al. .......... | 249/120 |
| 4,795,541 A | | 1/1989 | Hurd et al. .................. | 204/299 |
| 4,954,236 A | | 9/1990 | Kushner et al. ............. | 204/299 |
| 5,116,483 A | * | 5/1992 | Lander ..................... | 249/187.1 |
| 5,137,613 A | | 8/1992 | Brumley, Jr. et al. ....... | 204/299 |
| 5,209,831 A | * | 5/1993 | MacConnell ............... | 204/616 |
| 5,228,971 A | | 7/1993 | Brumley, Jr. et al. ....... | 204/299 |
| 5,938,906 A | | 8/1999 | Moi et al. .................... | 204/465 |
| 6,769,664 B2 | * | 8/2004 | Reed et al. .................. | 249/112 |

FOREIGN PATENT DOCUMENTS

| | | |
|---|---|---|
| EP | 0 350 962 | 1/1990 |
| EP | 0 304 195 | 12/1992 |
| EP | 0 334 615 | 11/1994 |

* cited by examiner

*Primary Examiner*—Monica A Huson
(74) *Attorney, Agent, or Firm*—Andrus, Sceales, Starke & Sawall, LLP

(57) ABSTRACT

A horizontal casting tray with one or more slidable blocks for sealing at least one open end of the tray is provided to accommodate the casting of solidifiable separation media in variable lengths for use in electrophoresis. Methods for using the casting device to prepare solidified medium having a concentration gradient are disclosed.

19 Claims, 7 Drawing Sheets

HORIZONTAL GEL CASTING DEVICE AND METHOD

FIELD OF THE INVENTION

The present invention relates to a device and method for providing separation media for use in a horizontal electrophoresis system.

BACKGROUND OF THE INVENTION

Horizontal electrophoresis has been an enduringly popular choice for separation of nucleic acids and proteins and offers several advantages over vertical electrophoresis. Generally, horizontal gels used as separation media are easier to cast than vertical gels. Further, thicker gels can be provided in a horizontal format than in a vertical system, and a lower concentration of separation medium, such as agarose, can be used in horizontal gels than in vertical gels allowing for better separation of high molecular weight molecules. Also, in a horizontal format, sample wells may be provided within the interior of the gel as well as at the top edge, increasing the number of samples that can be loaded per gel.

The typical system for casting horizontal gels utilizes a gel-casting tray with a flat bottom surface, two opposing parallel sides and two open ends that must be blocked at set points to retain the separation medium until the medium solidifies, resulting in a gel of limited dimensions. The open ends are usually sealed with an adhesive tape or sealed by the placement of casting gates in pre-cut grooves in the sidewalls and bottom surface of the tray. Whatever method is used, the gel is formed only in specific, predetermined lengths.

Several horizontal gel systems, in particular, catalog numbers HG-12, HLB-12, HG-20 and MG-10, available through Tyler Research Corporation, Alberta, Canada, utilize an adjustable gate-placement design. The design allows a casting gate to be placed into one of three placement grooves at pre-set lengths. Although the design increases the flexibility of a system in that it provides for some choice of length to be made, it is still limited to pre-determined lengths. Thus, there is a need for a horizontal gel-casting device that permits the selection of length from along a continuum of lengths.

A further disadvantage of systems with pre-determined gate settings is that each setting requires a groove cut in the sidewalls and the otherwise smooth bottom surface of the casting tray for gate placement. Because the grooves are machined for a tight fit with the casting gate, additional grooves add to the cost of manufacturing. Moreover, when a relatively longer gel is poured, the grooves cut in the bottom surface of the casting tray cause variation in gel thickness leading to possible distortion of the separation pattern in the gel.

Another limitation associated with using trays with only preset gel dimensions is that the preparation of a gradient gel, in which the concentration of agarose or other ingredients is varied from one end of the gel to the other, is not possible using existing casting tray systems with placement of casting gates only at the ends of the trays, and is not practical using systems with only a few pre-determined gate settings along the length of the tray. Gradient gels are advantageous when separating specimens containing macromolecules over a wide range of sizes. There is a need for a horizontal gel casting system that permits incremental increases, as desired, in the concentration of the separation medium along the length of the gel.

SUMMARY OF THE INVENTION

The present invention relates, in one aspect, to a device for providing horizontal gels wherein the length of the separation medium is selected from a continuum of possible lengths. Such a feature is beneficial in terms of more efficient use of materials, thus decreasing material costs, and in terms of more effective separation length in accordance with the samples to be analyzed. In another aspect, the invention relates to a method of using the device to produce gels of either a single concentration of separation medium or a gradient of concentrations of separation medium.

In its preferred form, the device comprises a casting tray with two opposing parallel sidewalls and two open ends wherein one end is sealed at any point along the length of the tray by a slidable block that acts as a dam to prevent fluid leakage.

Various other features, objects and advantages of the invention will be made apparent from the following description taken together with the drawings.

BRIEF DESCRIPTION OF THE DRAWINGS

The drawings illustrate the best mode presently contemplated of carrying out the invention.

In the drawings.

DETAILED DESCRIPTION OF THE INVENTION

Figure 1:
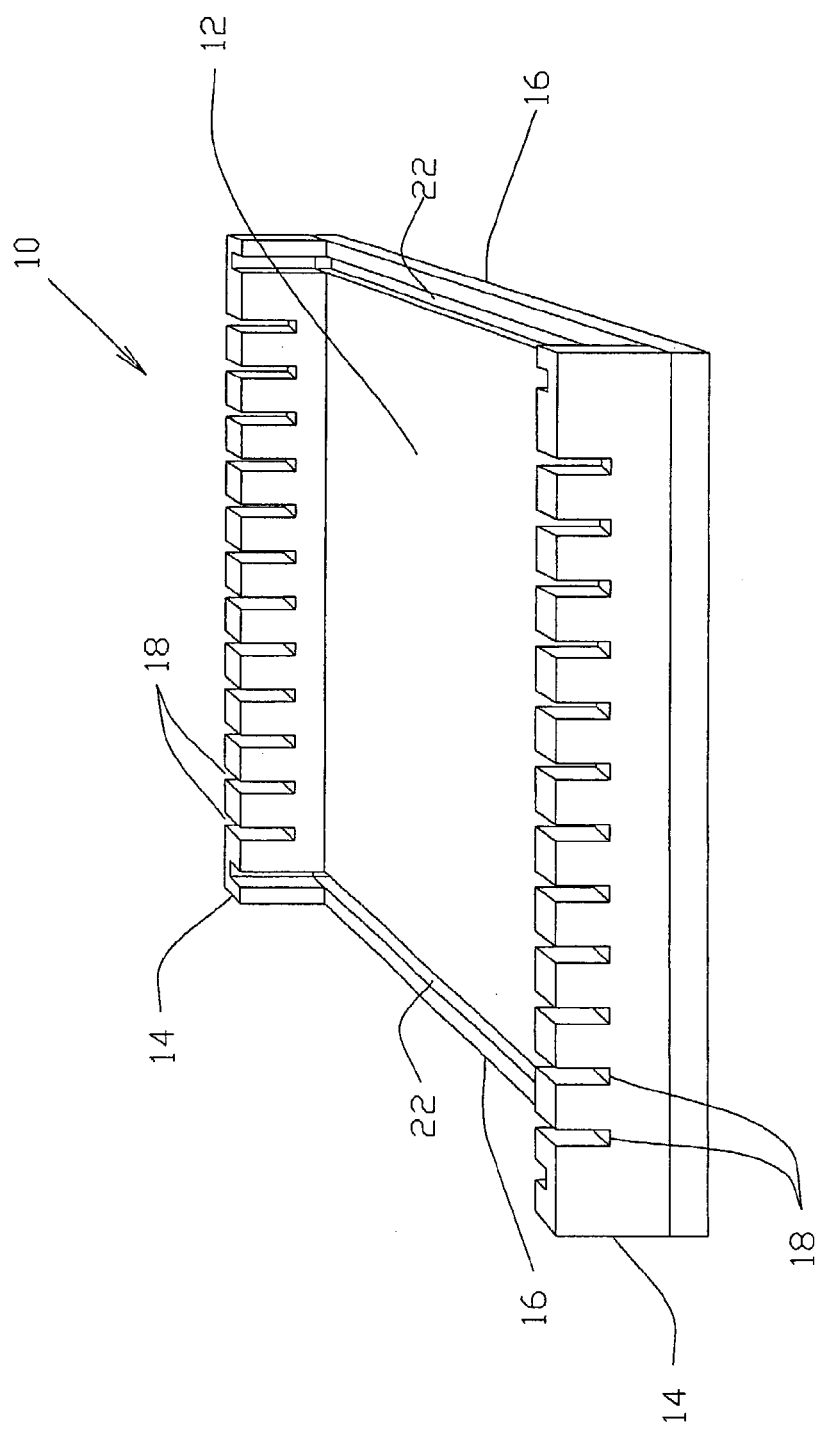
FIG. 1 is a perspective view of a conventional casting tray showing two opposing parallel sides and two open ends.

FIG. 1 is a perspective view of a conventional casting tray 10.

Figure 2:
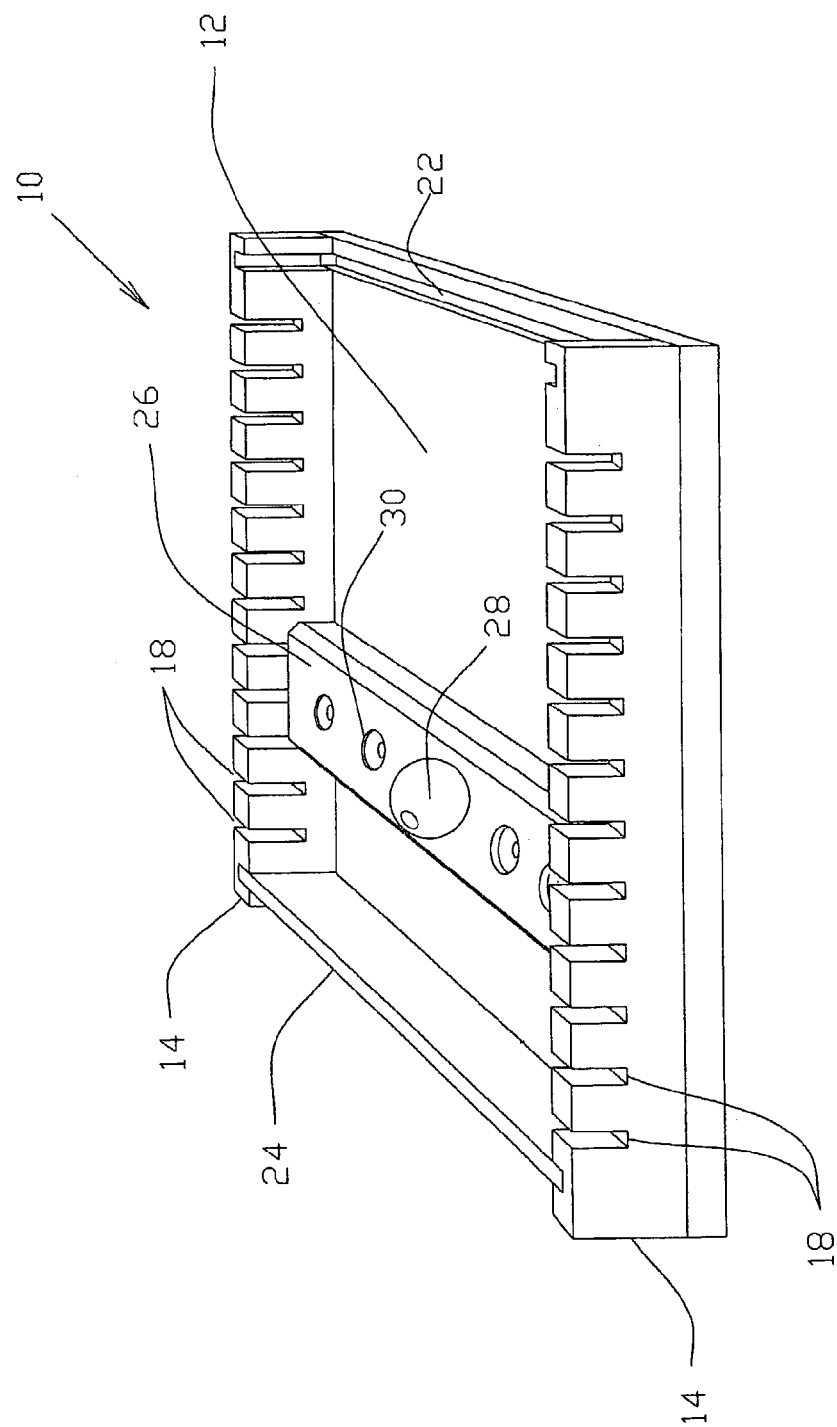
FIG. 2 is a perspective view of a casting tray showing one end sealed with a conventional casting gate and the other end sealed with a sliding block in accordance with a preferred embodiment of the invention.
Figure 7:
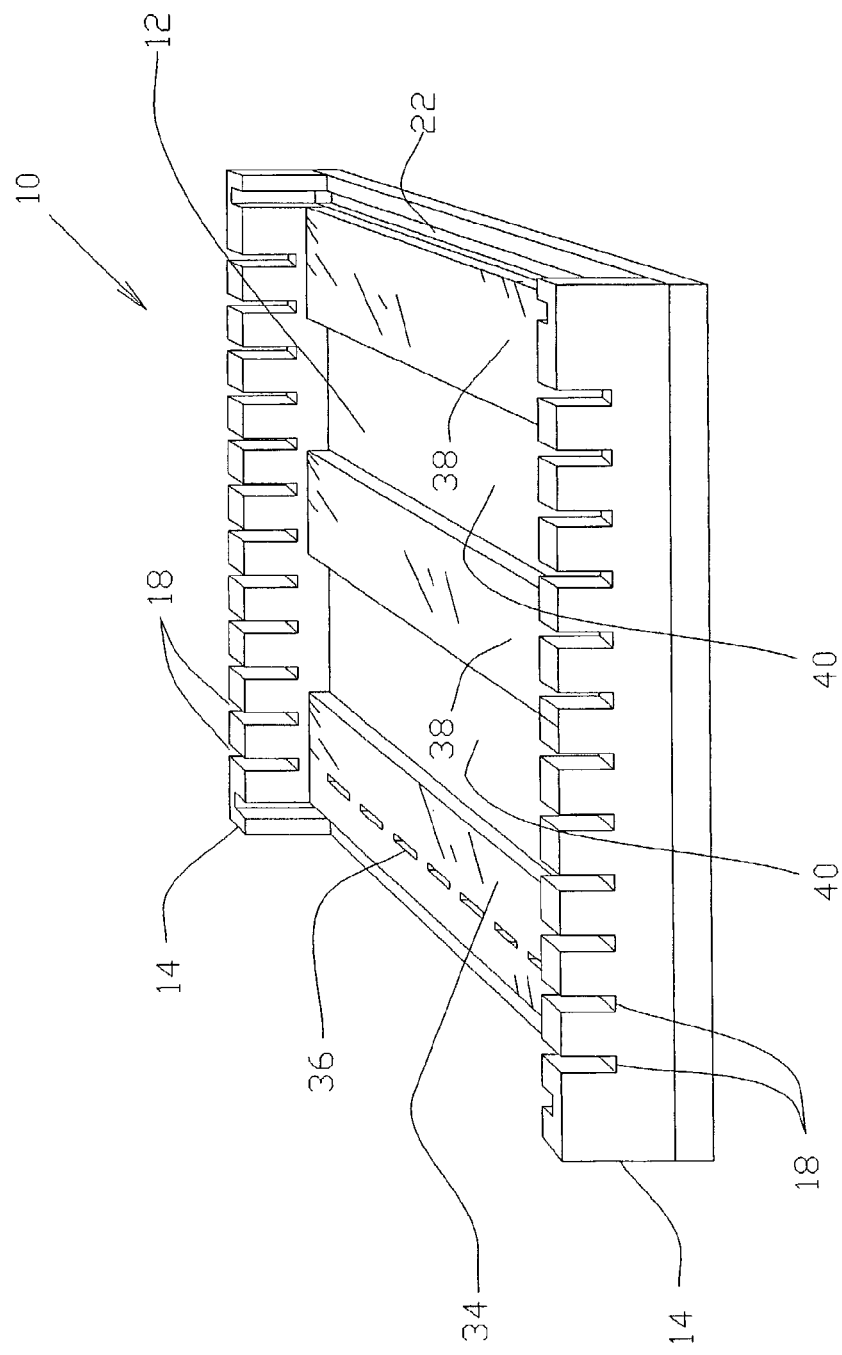
FIG. 7 shows the sections of solidified separation medium with voids in between the sections where the blocks had been placed.

Referring to FIG. 1, the casting tray 10 has a generally flat inner surface 12, two opposing parallel sidewalls 14 and two open ends 16. The casting tray 10 is preferably made of transparent plastic, such as polymethylmethacrylate or polymethylpentene, molded or machined. Alternatively, the casting tray 10 may be made of any material that would retain a flat surface 12 after repeated use, especially after exposure to molten agarose. The sidewalls 14 have one or more pairs of notches 18, molded or machined, for positioning one or more combs 20, shown in FIG. 3, for forming sample wells 36, as shown in FIG. 7. A groove 22 running across the surface 12 and into each opposing sidewall 14 serves for placement of a casting gate 24, as shown in FIG. 2. Preferably, the groove 22 for gate placement is located at each open end 16, but may be located at only one end 16, or may be placed at any other point along the length of the casting tray 10. Preferably, the groove 22 is precision machined or otherwise formed to create a fluid-tight fit with a casting gate 24.

The casting tray 10 can be made to any dimension with preferred dimensions comprising a width of at least four inches and a length of at least nine inches. For longer gels, the length of the casting tray 10 is preferably at least twelve inches, and more preferably, greater than fifteen inches. The depth of the sidewalls 14 is preferably at least one inch.

FIG. 2 is a perspective view showing the casting tray 10 with one open end 16 sealed by means of a casting gate 24 and the other sealed by a slidable block 26. The casting gate 24 is made of acrylic, aluminum, silicone rubber or any other material capable of forming a fluid-tight seal when placed within a receiving groove 22, and of retaining a substantially flat shape upon repeated use. The slidable block 26 is preferably made of a material with high thermal conductivity, such as aluminum, alumina, brass, or silver, or other suitable material, so that when molten agarose is used as a separation medium, heat is rapidly absorbed allowing the agarose to gel quickly and seal the edge adjacent the slidable block 26. Also, for some applications, for example when using a low concentration of agarose, chilling the block beforehand in a freezer or refrigerator can enhance gelling. Alternatively, the slidable block 26 may be made of any material or composite of materials that permits the formation of a fluid-tight seal.

Figure 6:
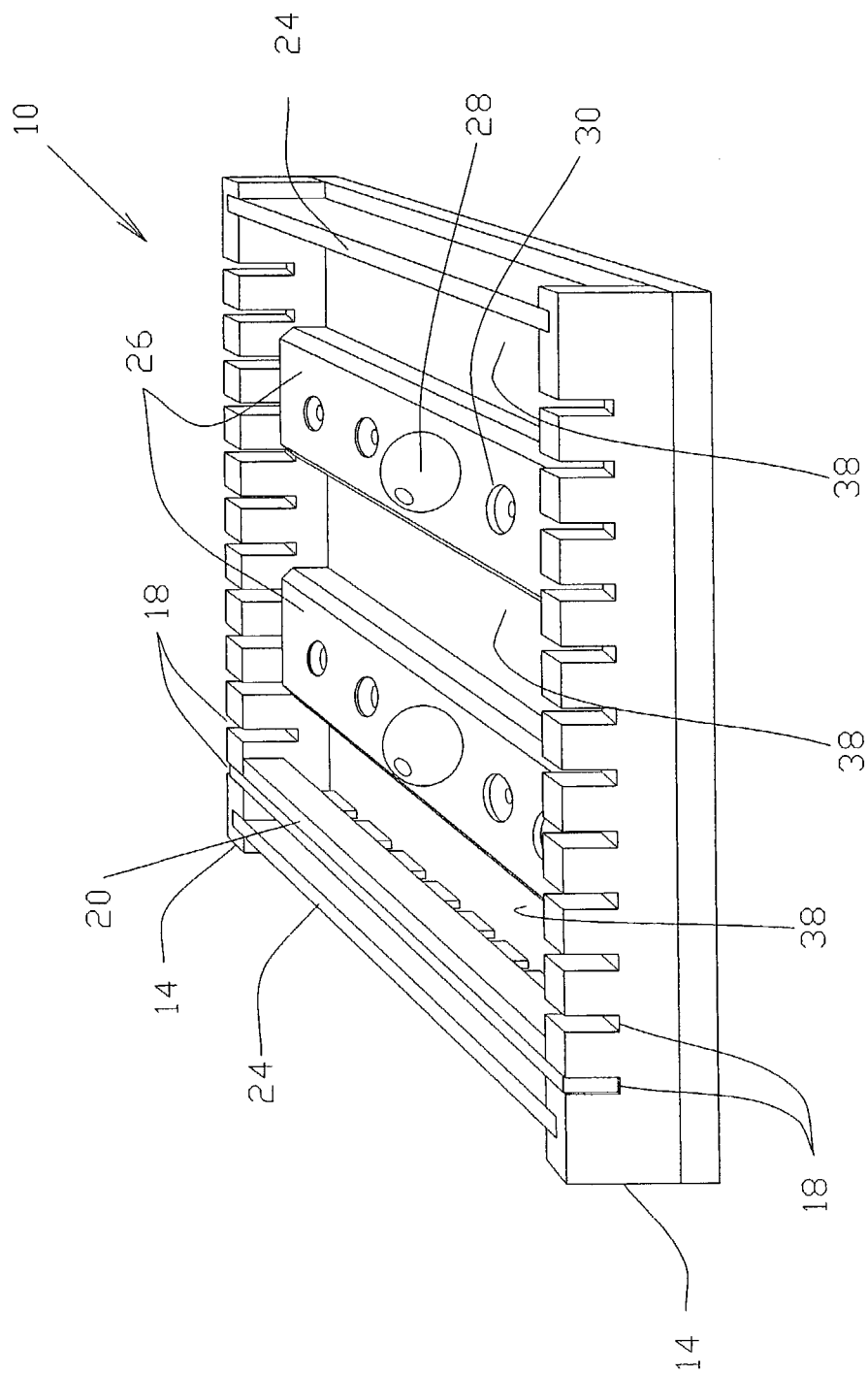
FIG. 6 shows one method of using the invention to form a step gradient gel by placing at least two slidable blocks in the casting tray at spaced intervals.

The slidable block 26 preferably has a knob 28 positioned anywhere along its length to facilitate sliding of the block 26. Alternatively or in addition, the slidable block 26 may be provided with one or more indents or depressions 30 to accommodate finger placement to facilitate sliding of the block 26. Likewise, a ridge or ridges on the top surface of the slidable block 26 can be used to facilitate sliding (not shown). The knob 28 or finger placement depressions 30 or ridges are not necessary for sliding the block 26, and thus, the block 26 may be formed without any feature to facilitate sliding. The knob 28 is preferred when using the block 26 to prepare step gradients as shown in FIG. 6. The slidable block 26 is preferably at least one-half inch in thickness.

Figure 3:
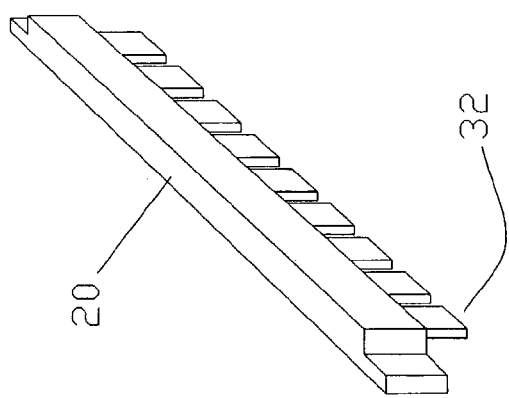
FIG. 3 is a perspective view of a conventional comb used to form sample wells in the gel in accordance with methods of using the invention.
Figure 5:
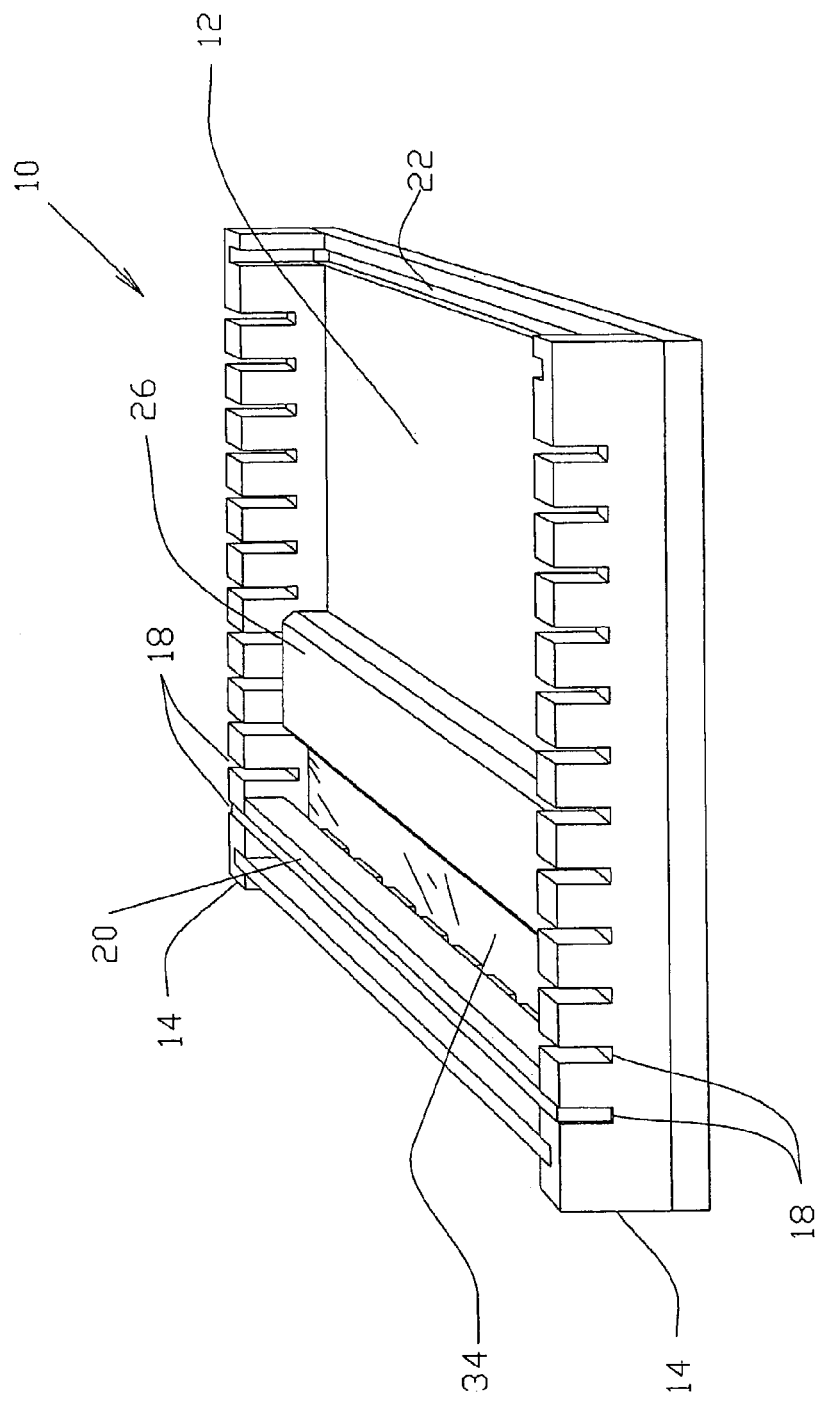
FIG. 5 is a perspective view of a casting tray filled with solidified separation medium and with the slidable block still in place.

Referring to FIG. 3, a perspective view of a conventional comb 20 used to form sample wells is shown. Combs 20 may be made of polycarbonate, acetal, polyetherimid, or other materials that are well known in the art for such applications. The teeth 32 of the comb 20 form slots or wells 36 in a separation gel 34, as shown in FIG. 5, to be filled with a sample preparation, calibration standards or other liquid specimens. The teeth 32 may be varied in thickness, width, and number as desired.

Figure 4:
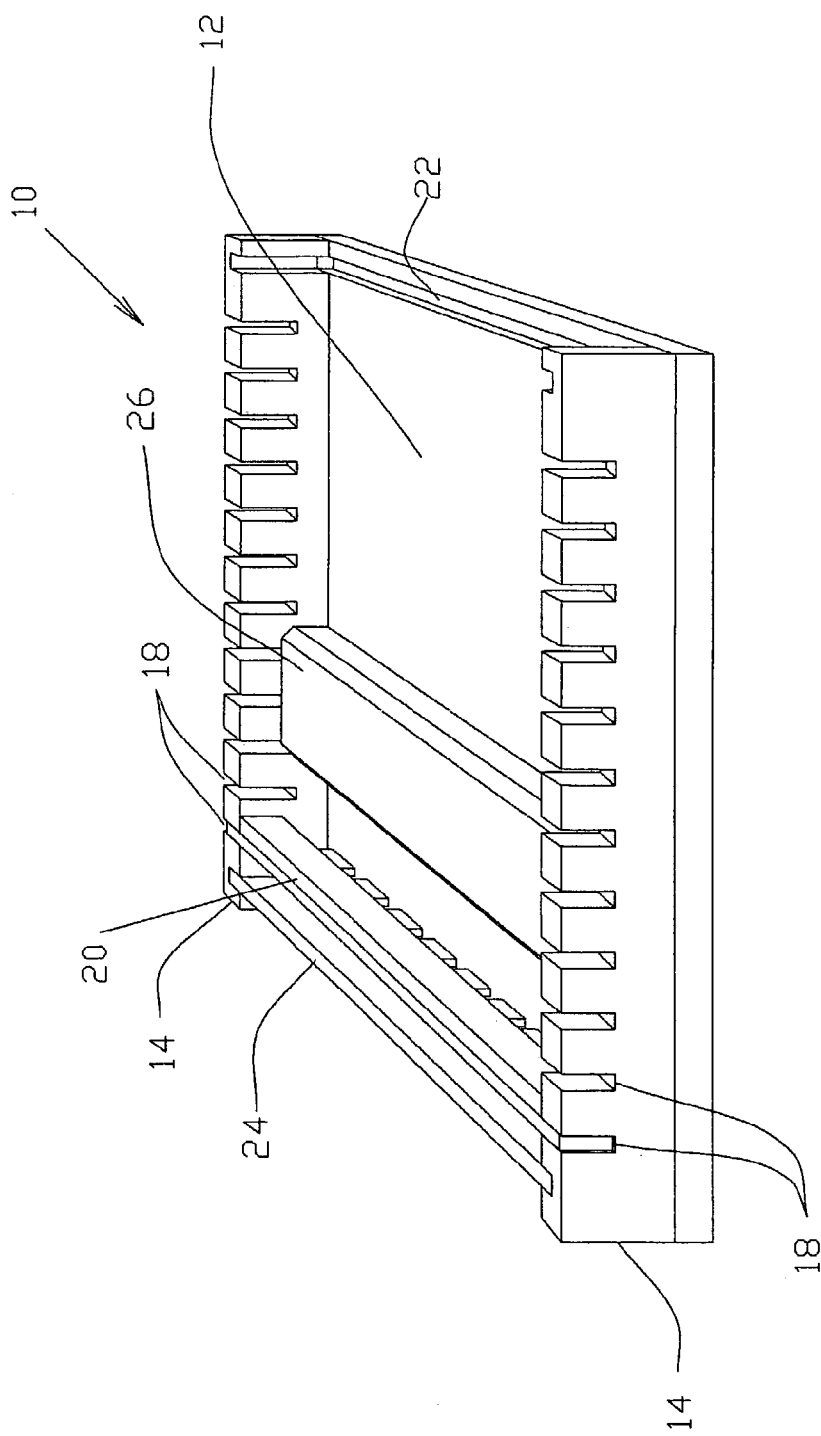
FIG. 4 is a perspective view of an empty casting tray sealed at each end showing the comb for forming sample wells in place in one set of placement notches.

A casting tray 10 with a casting gate 24, a slidable block 26, and a comb 20 in place within a set of notches 18 on opposing sidewalls 14 of the casting tray 10 is shown in FIG. 4. More than one comb 20 may be used, if needed, to form wells 36 within the body of a solidified separation medium 34 to accommodate increased sample numbers. The slidable block 26 is shown in close proximity to the comb to form a relatively short solidified separation medium, but the slidable block 26 may be placed anywhere along the length of the casting tray 10.

In use, preferably, one end 16 of the casting tray 10 is sealed with a casting gate 24 seated within a groove 22 in the casting tray 10, and the other end 16 is sealed with a slidable block 26, as shown in FIGS. 4 and 5. The length of the separation medium is varied by placement of the slidable block 26 along the length of the casting tray 10. Before or after a separation medium 34 is poured, one or more combs 20 are placed prior to solidification of the medium. When the medium 34 is set, the combs 20, casting gate 24, and slidable block 26 are removed for use in an electrophoresis device (not shown) as is conventional in the art. Alternatively the slidable block 26 can remain in the casting tray 10 and merely moved away from the bottom of the solidified separation medium to allow contact with an electrolyte-containing buffer. For such use, the slidable block 26 may be anodized or "hard-coated" to make the block 26 electrically non-conductive so that the base metal does not corrode electrolytically with repeated use.

To form a gradient gel, the slidable block 26 may be initially placed close to the end 16 that is sealed with a casting gate 24, as shown in FIG. 5, at a desired distance from the gate 24, and a volume of medium containing a first concentration of agarose or other separation component can be added. After the medium solidifies 34, the slidable block 26 can be moved incrementally as desired along the length of the casting tray 10, and separation medium of a second concentration can be added. These steps can be repeated as needed with additional concentrations of separation medium to form the desired gradient.

Alternatively, a simple "step" gradient is formed more quickly through the use of two or more slidable blocks 26. Referring to FIG. 6, the two open ends are sealed with casting gates 24, sealing tape, or any other suitable means of preventing leakage, and the slidable blocks 26 are placed with a spaces or gaps 38 of desired length between the two blocks and between the blocks and the casting gates 24. A different concentration of separation medium is poured into each of the gaps 38. Referring to FIG. 7, when the medium in the gaps 38 solidifies, the blocks 26 are removed, creating voids 40 where the blocks 26 had been. Solutions of separation medium with different concentrations from those previously used and from each other, are then poured into the voids 40. As an example, the gaps 38 formed by initial placement of two slidable blocks 26 as shown in FIG. 6, can be filled with solutions containing 0.5% and 1.5% agarose w/v respectively, then when the blocks 26 are removed as shown in FIG. 7, the voids 40 can be filled with solutions containing 1.0% and 2.0%, respectively. The blocks 26 may be independent of one another, or alternatively, two or more blocks may be connected, preferably by a handle attached to the top surface of each (not shown), in a fixed pattern.

Other embodiments, modifications, improvements and alternatives may be apparent to those skilled in the art. Such embodiments, modifications, improvements or alternatives are considered to be within the spirit of the invention.

Various alternatives and embodiments are contemplated as being within the scope of the following claims particularly pointing out and distinctly claiming the subject matter regarded as the invention.

I claim:

1. A method of forming and providing a separation medium comprising the steps of:
   (a) providing a casting tray with a substantially flat bottom surface defining a length, two opposing parallel sidewalls, a first open end and a second open end;
   (b) sealing said first open end;
   (c) selectively moving a slidable block along the length of the bottom surface of the casting tray to seal said second open end between the two opposing sidewalls with the slidable block at any point along the length of the casting tray; and
   (d) pouring said separation medium onto the bottom surface of the casting tray and allowing said separation medium to solidify, wherein the separation medium is supported by the bottom surface, the two opposing sidewalls, the sealed first open end and the slidable block.

2. The method of claim 1 wherein said first open end is sealed with a casting gate prior to step (c) and said casting gate is removed after step (c).

3. The method of claim 1 further comprising the step of placing at least one well-forming comb in the casting tray prior to step (c) and removing said at least one comb after step (c).

4. The method of claim 1 wherein said separation medium is agarose.

5. The method of claim 1 wherein said first open end is sealed with a second slidable block.

6. A method of forming a gradient gel comprising the steps of:
 (a) providing a casting tray with a substantially flat bottom surface defining a length, two opposing parallel sidewalls, a first open end and a second open end;
 (b) sealing said first open end;
 (c) selectively moving a slidable block along the length of the bottom surface of the casting tray to seal said second open end between the two opposing sidewalls with the slidable block at a point spaced from the first open end of the casting tray;
 (d) pouring a separation medium of a first concentration onto the bottom surface of the casting tray between the slidable block and the sealed first open end and allowing said separation medium to solidify;
 (e) moving the slidable block away from the solidified medium along the length of casting tray at a desired increment;
 (f) pouring a second separation medium of a second concentration onto the bottom surface of the casting tray and into the space between the solidified first medium and the slidable block;
 (g) allowing the second separation medium to solidify; and
 repeating steps (e) through (g), adding additional concentrations of separation medium as needed to form a gel having a concentration gradient.

7. The method of claim 6 further comprising the step of placing a well-forming comb in the casting tray prior to step (c) and removing the comb at some point after step (c).

8. The method of claim 6 further comprising the step of sealing said first open end with a casting gate prior to step (c) and removing the casting gate at any point after step (c).

9. A method of forming a gradient gel comprising the steps of:
 (a) providing a casting tray with a substantially flat bottom surface, two opposing parallel sides, a first open end, and a second open end;
 (b) sealing said first and second open ends;
 (c) selectively placing at least two slidable blocks along the length of the flat bottom surface of the casting tray, the slidable blocks being selectively movable along the length of the bottom surface of the casting tray and capable of preventing leakage of a separation medium within said casting tray, wherein the at least two slidable blocks are place at spaced intervals between the two opposing parallel sides within the casting tray;
 (d) simultaneously providing separation media of different concentrations onto the flat bottom surface of the casting tray, one medium into each space within the casting tray created by the placement of said at least two slidable blocks, and allowing said media to solidify while supported on the flat bottom surface of the casting tray;
 (e) removing said at least two slidable blocks; and
 (f) providing additional separation medium of different concentration from those used in step (c) and, if more than one medium is added, of different concentrations from each other, onto the flat bottom surface of the casting tray and into voids remaining upon removal of the slidable blocks, and allowing said additional separation medium or media to solidify while supported on the flat bottom surface of the casting tray;
 wherein a gel having a discontinuous gradient of increasing concentrations of separation media is formed on the flat bottom surface of the casting tray.

10. The method of claim 9 further comprising the step of placing a well-forming comb in the casting tray prior to step (c) and removing the comb at any point after step (c).

11. The method of claim 9 further comprising the step of sealing said first and second open ends with casting gates prior to step (c) and removing the casting gates at any point after step (c).

12. The method of claim 9 wherein said separation media comprise agarose.

13. A device for horizontal casting of a separation medium comprising:
 a casting tray with a substantially flat bottom surface defining a length, two opposing parallel sidewalls, a first open end that is sealed with a casting gate or with sealing tape prior to casting the separation medium, and a second open end; and
 a slidable block in contact with each of the parallel sidewalls and movable along the length of the bottom surface of the casting tray for sealing the second open end at any point along the length of the casting tray to selectively vary the length of the separation medium during casting,
 wherein the flat bottom surface of the casting tray contacts and supports the separation medium such that the separation medium is supported by the flat bottom surface, the sidewalls, the sealed first open end and the slidable block during casting.

14. The device of claim 13 wherein the two opposing parallel sidewalls each contain a plurality of aligned notches for selective placement of at least one well-forming comb.

15. The device of claim 13 wherein the slidable block is aluminum.

16. The device of claim 13 wherein said slidable block is equipped with a knob or handle to facilitate movement.

17. The device of claim 13 wherein said slidable block has at least one depression, indent or ridge for finger placement.

18. The device of claim 13 wherein said length of the casting tray is at least nine inches.

19. A device for horizontal casting of a separation medium comprising:
 a casting tray with a substantially flat bottom surface defining a length, two opposing parallel sidewalls, a first open end and a second open end;
 a first slidable block in contact with each of the parallel sidewalls and movable along the length of the bottom surface of the casting tray for sealing the second open end at any point along the length of the casting tray to selectively vary the length of the separation medium during casting; and
 a second slidable block for sealing the first open end of the casting tray prior to casting the separation medium,
 wherein the flat bottom surface of the casting tray contacts and supports the separation medium such that the separation medium is supported by the flat bottom surface, the sidewalls, the first slidable block and the second slidable block during casting.

* * * * *